(12) United States Patent
Bodily

(10) Patent No.: US 6,620,626 B1
(45) Date of Patent: Sep. 16, 2003

(54) ANTIGEN DETECTION DEVICE AND METHOD

(75) Inventor: Gary R. Bodily, Logan, UT (US)

(73) Assignee: Mission Research Corp., Santa Barbara, CA (US)

( * ) Notice: Subject to any disclaimer, the term of this patent is extended or adjusted under 35 U.S.C. 154(b) by 294 days.

(21) Appl. No.: 09/636,772

(22) Filed: Aug. 9, 2000

(51) Int. Cl.[7] .................... G01N 33/53; G01N 35/558; G01N 35/543
(52) U.S. Cl. .................. 436/518; 436/501; 436/512; 436/536; 436/525; 435/7; 435/805; 435/810; 422/55; 422/56; 422/57; 422/58; 422/68.1; 422/69
(58) Field of Search ................. 422/55–58, 68.1, 422/69, 56, 57; 435/7, 805, 810; 436/501, 512, 518, 523, 536, 525

(56) References Cited

U.S. PATENT DOCUMENTS

| | | | | |
|---|---|---|---|---|
| 4,857,453 A | * | 8/1989 | Ullman et al. ................. | 435/7 |
| 4,981,786 A | * | 1/1991 | Dafforn ......................... | 435/7 |
| 5,236,826 A | * | 8/1993 | Marshall ..................... | 435/7.92 |
| 5,356,782 A | * | 10/1994 | Moorman et al. ........... | 435/7.9 |
| 5,820,826 A | * | 10/1998 | Moorman et al. .......... | 422/104 |
| 5,874,216 A | * | 2/1999 | Mapes .......................... | 435/6 |
| 6,046,057 A | * | 4/2000 | Nazareth et al. ............ | 436/514 |

* cited by examiner

Primary Examiner—Long V. Le
Assistant Examiner—Changhwa J Cheu
(74) Attorney, Agent, or Firm—Laura N. Tunnell

(57) ABSTRACT

A monitor having a hollow semipermeable casing with a test strip is agitated in a sample volume of suspect liquid. The monitor is partially filled with tiny colored beads confined to its interior by the size of the openings in the semipermeable structure. Adhered to the beads are antibodies matched to the antigen characterizing the suspect substance. The test strip is segregated into collection and control regions. Antibodies matched to the suspect antigen are adhered only to the collection region. If the sample fluid contains the suspect substance, it will bind to both the bead antibodies and the collector antibodies, resulting in an accumulation of colored beads in the collection region but not the control region. A significant color differential between the two is a positive indication of the suspect substance. This invention has significant potential in screening for the date rape drugs, GHB and rohypnol.

5 Claims, 8 Drawing Sheets

Antigen of Interest Present (130)

Control Region (50)　　　　Collection Region (40)

Representation of test strip configuration in the presence of the antigen of interest. Note the antibody / bead pairs are randomly oriented throughout the control region of the test volume and are regularly oriented throughout the test region.

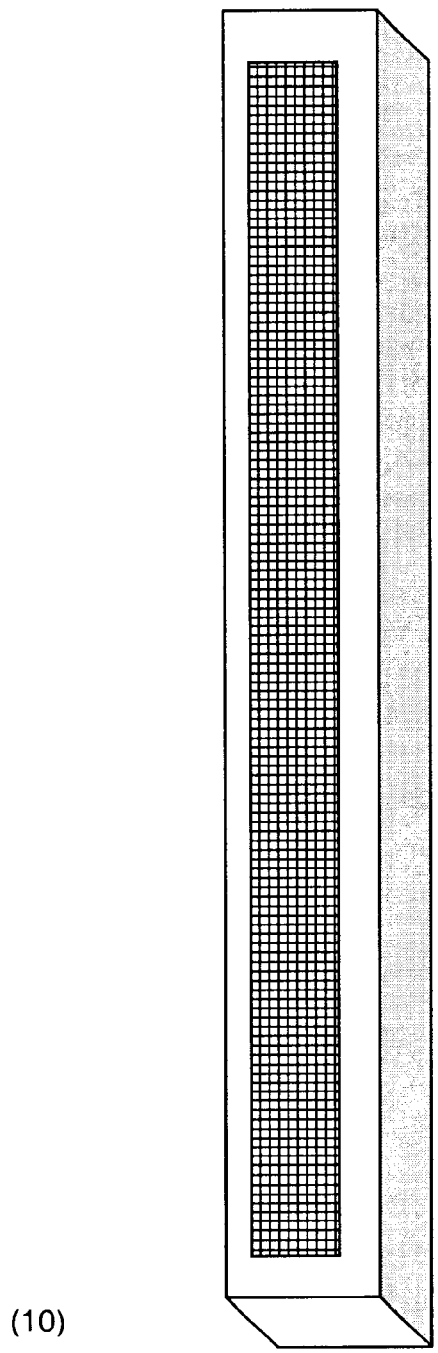
Figure 1: Isometric view of monitor.

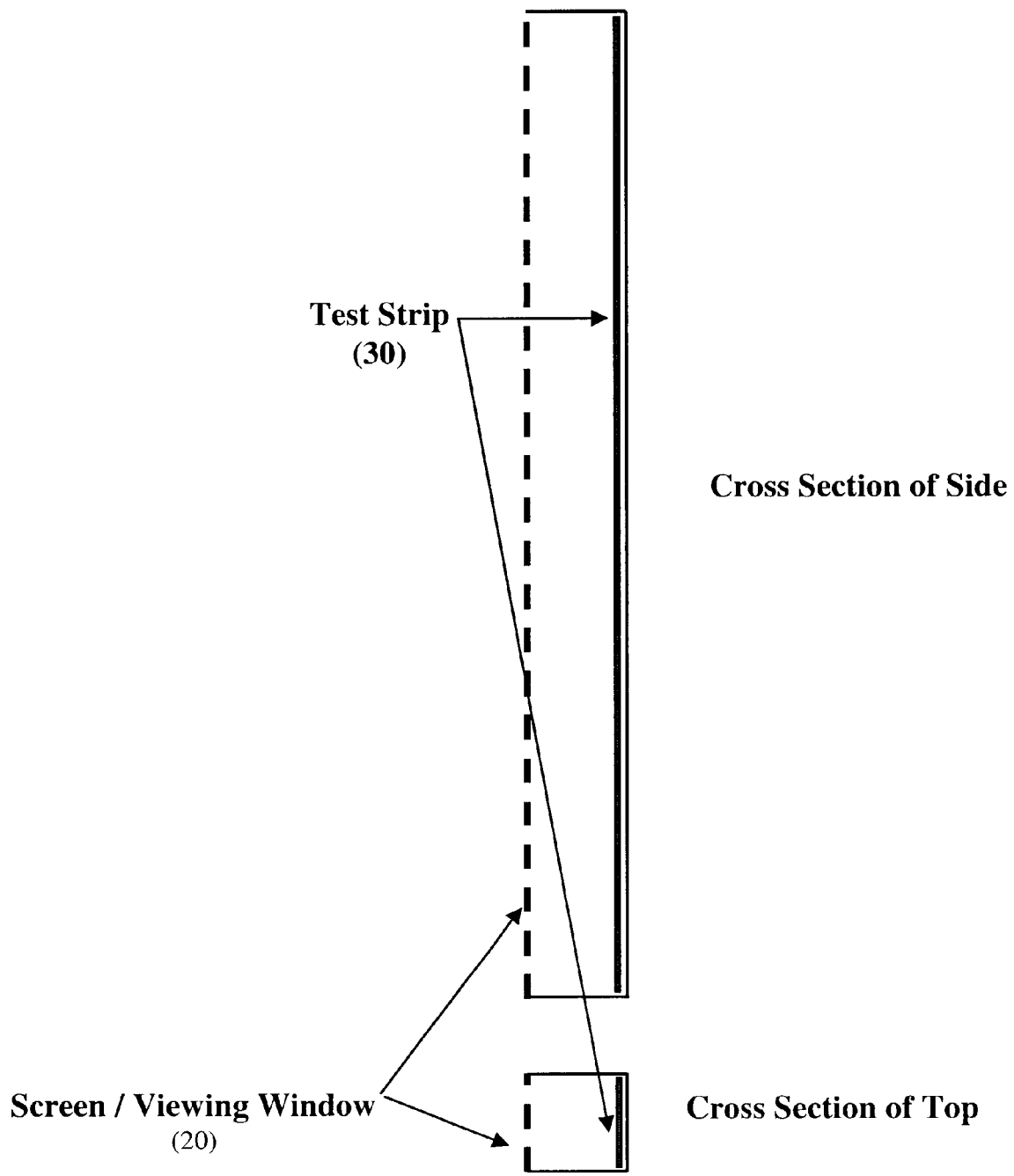
Figure 2: Cross sections of monitor interior.

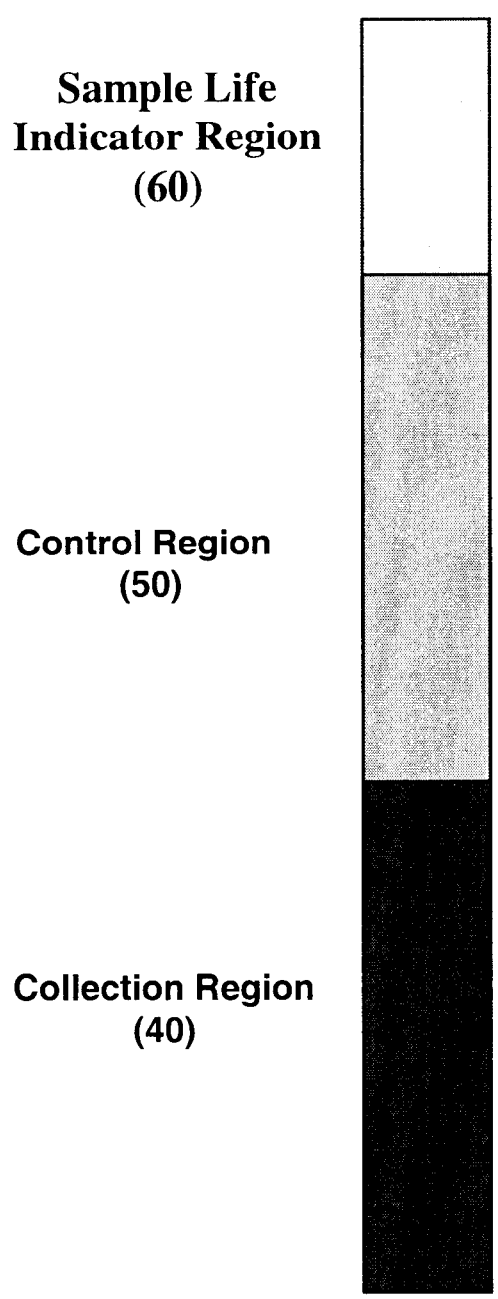
Figure 3: Top view of test strip.

— Antigen of Interest (70)

● Tagged Bead (80)

Y Antibody Matched to Antigen of Interest (90)

⚇ Matching Antibody with Bead Attached (100)

Y̓ Neutral Antibody (Not Matched) (110)

Figure 4: Chart listing the icon definitions of Figures 5 and 6.

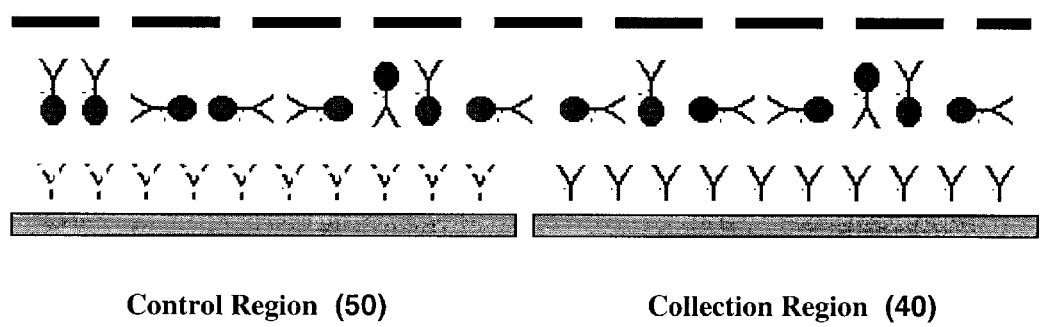
Figure 5: Representation of test strip configuration in the absence of the antigen of interest. Note the antibody / bead pairs are randomly oriented throughout the entire test volume.

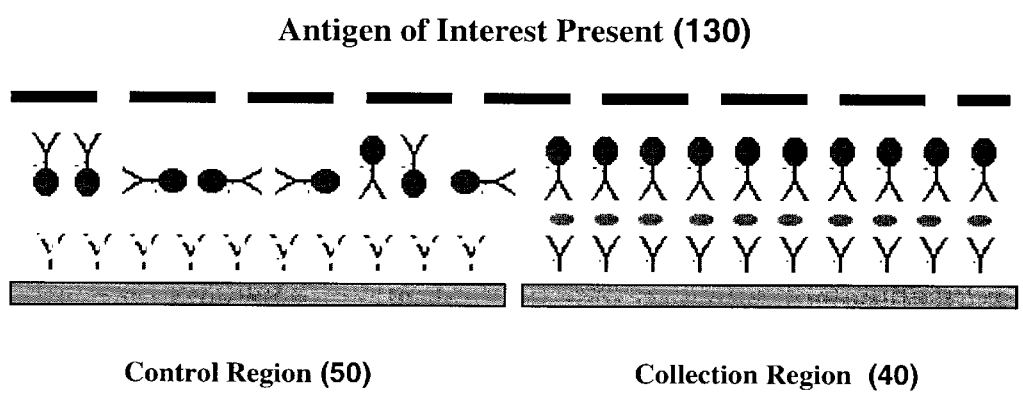
Figure 6: Representation of test strip configuration in the presence of the antigen of interest. Note the antibody / bead pairs are randomly oriented throughout the control region of the test volume and are regularly oriented throughout the test region.

Figure 7: Small antigens have limited space for attachment with antibodies.

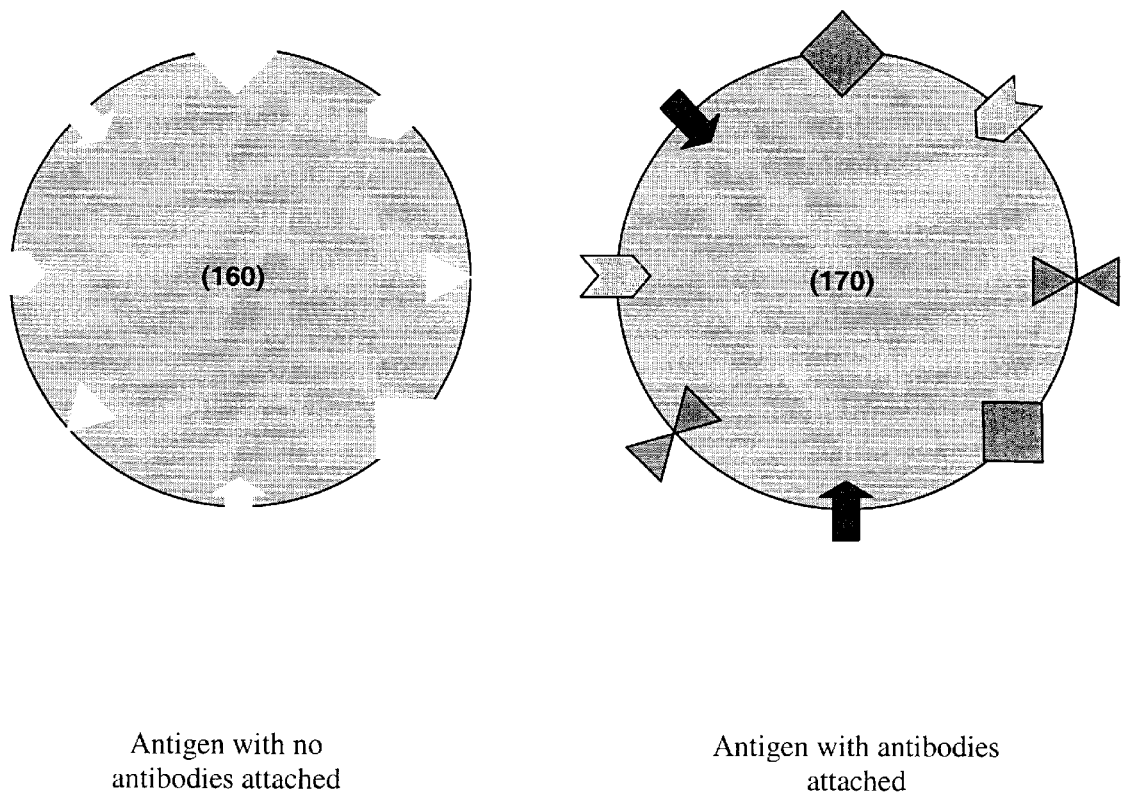
Figure 8: Large antigens have ample space for attachment with antibodies.

ANTIGEN DETECTION DEVICE AND METHOD

BACKGROUND OF THE INVENTION

1. Field of the Invention

The present invention relates generally to fluid monitors for detecting the presence of a substance in a fluid and, more particularly, to a method and device for detecting the presence of an antigenic substance in a fluid.

2. Prior Art

Determining the presence of a suspect substance in a liquid sample is a problem that has been addressed by many technologies. The methodology most commonly used for detecting such substances involves using one or more antibodies that have been matched to an antigenic binding site or sites characterizing the suspect substance. These matched antibodies must be colored or otherwise tagged in a way that is physically distinguishable from some type of control in which the antigen/antibody reaction has been prevented from taking place.

Such prior art immunological detection procedures vary somewhat, but generally involve isolating a small portion of the liquid sample, exposing it to the tagged antibody, and comparing the resultant reactions (or lack thereof) with a control. Notwithstanding false readings, a significant difference between the sample and the control indicates the presence of the suspect antigen in the liquid.

Methods for making and harvesting monoclonal or polyclonal antibodies that have a specific avidity for a given antigen are well known in the art. Prior art detection methodologies employing antigen-antibody binding require a multiple stage analysis. This may be accomplished by either directing the sample fluid along a flow path from the reaction region to a "developer" region, or by physically moving the sample from one region to another. Such methods have presented many problems. The challenge has been to design a system with sufficient test sample fluid throughput so that it is possible for the required reactions to occur. Such devices must be discarded after only one use. There remains a need for a detection device and method that can be used to monitor a fluid for the presence of a substance and which can be reused until the substance is detected.

SUMMARY

The present invention is a device for detecting the presence of an antigen of interest in a liquid. The device is comprised of a hollow casing having an interior volume defined by the hollow casing. A plurality of beads is disposed within therein fills the interior volume. The beads have a measurably distinguishing attribute associated therewith, preferably a distinctive color, and have antibodies attached thereto that are capable of binding to the antigen of interest. A portion of the casing is a permeable screen enabling the diffusion of both the test fluid and the antigen therethrough but retaining the beads within the interior volume. A test strip disposed on an interior surface of the casing comprises a collection region disposed on a portion thereof. The collection region has at least one antibody capable of binding to the antigen of interest and incapable of binding to the beads attached thereto. When the device is dipped into the liquid to be tested, the liquid enters the interior volume through the permeable screen and if the antigen of interest is present within the fluid-filled interior volume of the casing, the beads become attached to the collection region by virtue of their common bond with the antigen of interest, thereby concentrating the colored beads in the collection region. The strip further includes a control region disposed thereon having the ability to retain its original state regardless of the presence or absence of the antigen of interest. The phrase "control region", as used herein, means a region of the test strip lacking antigen-specific antibodies bound thereto. It provides a comparison with the collection region so that a reasonable determination of the presence of the suspect antigen can be made.

It is a first object of this invention to provide a small, simple device that can be easily manufactured, is usable by any member of the general public, and provides a reliable test for the presence of a specific antigen in a liquid sample.

It is a further object of the invention to provide a device meeting the above objective that can be used to monitor a fluid for the presence of the specific antigen over an extended period of time.

An example of a current application of the present monitoring device and method for solving a current social problem is the monitoring beverages for the presence of GHB or rohypnol, the so called date rape drugs. Other applications include medical analysis (i.e., detecting a substance in various body fluids), drug testing/screening, municipal water testing and pregnancy testing. The monitoring device is also suitable for biological or chemical warfare applications in that it can be designed to test for particular pathogens or chemicals suspected or known to be used in such situations. It is particularly useful to hikers and other outdoor enthusiasts for the screening of water supply sources.

The present device is not a flow system. Although the sample fluid must enter the interior volume of the device in order to be tested for the presence of a substance, the fluid does not have to be routed along a prescribed flow path or be transported into a developer region or be rinsed or washed in order for the device to operate. Thus, questions of fluid sample "throughput" that plague the prior art are rendered moot with the present device. The present device is unique in that it continuously monitors any liquid in which it is placed until such time as the indicator system either undergoes denaturization (i.e., becomes inoperable as a detector), or detects the suspect antigen. Accordingly, the present monitoring device can be used to test several different volumes of liquid, such as, for example, alcoholic beverages, in real time during its effective lifetime. Further, the present device will not introduce any reactants, either toxic or otherwise, into the sample being tested. In the case of a positive reading, the device serves to contain the suspect liquid as evidence of the presence of an antigen, which may indicate tampering, or for subsequent confirmatory analysis.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

BRIEF DESCRIPTION OF THE DRAWINGS

FIG. 1 shows an isometric view of the monitor.

FIG. 2 shows a side and top cross section of the monitor interior.

FIG. 3 shows a top view of the monitor test strip.

FIG. 4 is a chart defining and illustrating the icons used in FIGS. 5 and 6.

FIG. 5 is a notional depiction of the test strip configuration in the absence of the antigen of interest. Note the antibody/bead pairs are randomly oriented throughout the entire test system.

FIG. 6 is a notional depiction of the test strip configuration in the presence of the antigen of interest. Note the antibody/bead pairs are randomly oriented throughout the control region of the test volume and are regularly oriented throughout the test region.

FIG. 7 illustrates the correlation between small antigen size and limited capacity for multiple binding sites.

FIG. 8 illustrates the correlation between large antigen size and expanded capacity for multiple binding sites.

REFERENCE NUMERALS

10—hollow casing
20—screen/viewing window
30—test strip
40—collection region
50—control region
60—sample life indicator region
70—antigen of interest
80—tagged bead
90—antibody matched to antigen of interest
100—matched antibody with bead attached
110—neutral (unmatched) antibody
120—test strip configuration in the absence of the antigen of interest
130—test strip configuration in the presence of the antigen of interest
140—small antigen with no antibodies attached
150—small antigen with antibodies attached
160—large antigen with no antibodies attached
170—large antigen with antibodies attached

DESCRIPTION OF THE PREFERRED EMBODIMENTS

The present invention is a monitor that can be used to test for the presence of a suspect substance in a volume of liquid over a period of several hours. It is operationally simple, easy to manufacture and can be used by anyone. Moreover, in the event that the suspect substance is detected, the monitor can house and preserve the contaminated sample for subsequent closer inspection or as evidence of tampering.

Several views of the monitor are shown in FIGS. 1, 2, and 3. The casing 10 defines a hollow interior with a test strip 30 disposed within the hollow interior. A portion of the casing 10 is permeable to a fluid and a substance to be detected in the fluid. For example, a portion of the casing may include an opening covered with a screen 20. In the preferred embodiment, the screen 20 also functions as a viewing window. The test strip 30 comprises a collection region 40, a control region 50, and an optional sample life indicator region 60.

FIG. 4 defines and illustrates icons used in FIGS. 5 and 6 in which a notional representation of the operation of the test strip 30 is shown. The collection region 40 of the test strip 30 is covered with antigen-specific antibodies 90 that have specific binding avidity and selectivity for the antigen of interest 70, which antibody characteristically associated with the substance to be detected. The terms, "antigen of interest", and "suspect antigen", are used interchangeably herein to denote an antigen that is characteristically associated with a substance to be detected. The control region is either barren or is covered with neutral antibodies 110 (i.e., antibodies that will not bind to the antigen of interest). Beads 80, measurably distinguishable from their immediate surroundings, are attached to the matched antibodies 100. As used herein, the term "matched antibodies" refers to antibodies that selectively bind to an antigen that is characteristically associated with a substance being detected.

The interior volume of the hollow casing 10 is filled with a plurality of the bead/matched antibody units. The term "substrate antibodies", as used herein, is used to denote the matched antibodies attached to the collector region of the test strip. Matched antibodies that are attached to the beads are referred to as "bead antibodies". The beads 80 are designed to be small, so that they move in a fluid fashion and are homogeneously distributed throughout the interior volume, and yet large enough to be confined to the interior volume by the size of the screen apertures in the casing. In the preferred embodiment, the bead's size is comparable to a dust particle, with the screen aperture size being slightly smaller than the bead. In addition, the beads should have neutral buoyancy in the fluid being tested to prevent aggregation of the beads due to floating or settling within the interior volume of the monitor.

When the monitor is placed in a test volume containing the suspect liquid, the antigens of interest 70 in the suspect liquid penetrate the permeable portion of the casing (eg: the screen 20) and bond to both the bead antibodies and the antibodies in the collection region as indicated at numeral 130. This will result in an accumulation of beads in the collection region as compared with the control region. In the preferred embodiment, color is the distinguishably measurable attribute of the beads. Accordingly, a significant color differential between the control region and the collection region of the test strip is an indication of the presence of the antigen of interest. The converse (i.e., no color difference) is true if the suspect antigen is not present as indicated at 120.

FIGS. 7 and 8 illustrate another important consideration with regard to this invention. The antigen of interest must adhere to both the substrate antibodies and the bead antibodies. If the antigen is small, as illustrated in FIG. 7 at numerals 140 and 150, then the size of the antigen itself restricts the number of potential attachment site pairs that will allow simultaneous binding to both the bead and substrate antibodies. Accordingly, the larger the size of the antigen, as indicated in FIG. 8 at numerals 160 and 170, the less this is true. This potential limitation connected with the size of the suspect antigen must be considered in the design of the system.

The aforementioned "sample life region" 60 is simply an indicator that the operability of the test strip has not degraded. The operation of the sample life region 60 relies on a matched antigen/antibody pair that is totally independent of the components used to detect for the presence of the suspect antigen. It too is covered with a substrate impregnated with antibodies matched to a second set of bead/antigen pairs. In this case, however, the antigens have been adhered to this second set of beads so that they will remain attached to the sample life region if the monitor is still operational. When this ceases to occur, one can assume that the entire system has become denatured or otherwise succumbed to environmental conditions.

The method and device disclosed herein can achieve a higher degree of selectivity, thereby reducing the false positive rate, by utilizing several sets of "substrate antibody/bead antibody" pairs. For instance, the collection area may be further segregated into three or four areas, each having a different antibody specific to the antigen of interest, while the bead antibody remains of one type. If a uniformity of color occurs among all of the segregated areas and is distinctly different from the color of the control area, then the criteria for a true positive reading has been met. Conversely, the beads could be segregated into three or four groups, each group having its own color and its own antibody matched to the antigen of interest, while keeping the substrate antibody of one type. Uniformity in the distribution of colors in the collection area would then act as an alert to the presence of the suspect antigen. A multitude of such schemes can be envisioned, if necessary, depending upon the properties of the particular antigen under scrutiny.

The operation of this device is extremely simple. One need only place the monitoring device in a liquid, agitate the liquid, and inspect the device for any color abnormalities between the different areas of the test strip. A significant accumulation of colored beads should be present in the "sample life indicator" area if the test strip so equipped. If the test strip is of the single bead antibody/single substrate antibody embodiment, a significant color difference between the collection area and the control area of the test strip is an indication of the presence of the suspect antigen, and therefore of the suspect substance in the liquid sample. If the test strip is of the single bead antibody/multiple substrate antibody embodiment, then a uniform covering of colored beads between all collection areas is necessary for a positive reading. If the test strip is of the multiple bead antibody/single substrate antibody variety, then a uniform mix of colored beads between all collection areas is necessary for a positive reading.

The foregoing disclosure describes the operation of embodiments of the monitor for personal use, i.e. in beverages, testing the purity of drinking water, etc. In such embodiments, the test region of the monitor is designed to be observed or "read" by relatively untrained people by visual inspection. In industrial applications, the test strip is conveniently read by means of connecting the strip via a suitable interface with an automated detection system.

The basic operation of an automated substance detection system is the same as for a personal use system. The reaction is the same (i.e., colored beads accumulate and adhere to the collector region of the test strip) but the method of monitoring the test strip is different. For instance, a hiker or camper would use a monitor device in accordance with the present invention to test water from a stream for the presence of pathogens by visual inspection of the monitor whereas monitoring the same water for public use would be done by an automated system. Such an automated monitoring system might have a larger test reservoir, a more convenient placement of the screen, as well as larger collection and control regions. Nevertheless, a comparison of the relative accumulation of beads in the collection area as opposed to the control area must still be made. The comparative function can be performed by suitable instrumentation, minimizing the need for human attention.

The monitoring of such a bead distribution differential, indicating the presence of an antigen, could be done in many ways. The most literal embodiment would be to simply monitor for a color change by means of a video camera or a balanced dual-channel colorimeter. A further embodiment of the device might include a bead characterized by a distinctive fluorescence emission rather than color. This property could be monitored by any number of light sensing devices. Or, the testing area could be chosen to be a reflective surface whose reflective properties are modified in a measurable way when beads bind to, and coat, the collector area(s) of the test strip.

Still further embodiments could include using laser stimulation of the collector surface(s) and observing a change in the differences in the resulting photo-acoustic signatures. Evanescent waves, either optical or acoustic, may be employed wherein an initially combined wave is split up, sent over both surfaces of the test strip, and recombined. Detection of a resultant phase shift between the recombined segments would indicate a bead distribution differential over the pertinent areas of the test strip surfaces.

The present invention provides a simple, inexpensive device that can be used by an untrained person to continuously monitor a liquid volume in order to detect the presence of a given substance therein. While particular embodiments of the present invention have been illustrated and described, it would be obvious to those skilled in the art that various other changes and modifications can be made without departing from the spirit and scope of the invention. For example, the system can be automated so that and very large liquid volumes, such as a city's water supply, can be monitored for the presence of suspect substances and/or pathogens. It is therefore intended to cover in the appended claims all such changes and modifications that are within the scope of this invention.

I claim:

1. A monitoring device for detecting the presence of a substance in a fluid, wherein the substance is characterized by the presence of at least one substance-specific antigen which selectively binds lo an antigen-specific antibody, comprising:
   1. a casing enclosing an interior volume wherein a portion of said casing has a plurality of apertures therein, enabling the fluid and the substance to pass therethrough;
   2. a test strip having a collector portion and a control portion disposed within said interior volume;
   3. a plurality of beads, each bead having a diameter that prevents the bead from passing through said apertures of said casing, and a surface with antigen-specific antibodies affixed thereto, said plurality of heads being movably disposed within said interior volume; and
   4. antigen-specific antibodies affixed to said collector portion of said test strip.

2. The monitoring device or claim 1 wherein said beads each have an identical visually distinguishable characteristic.

3. The monitoring device of claim 2 wherein said visually distinguishable characteristic is color.

4. The monitoring device of claim 1 wherein said beads arc larger than said apertures.

5. The monitoring device of claim 1 wherein at least a portion of said casing is optically transparent.

* * * * *